US007635474B2

(12) United States Patent
Daly et al.

(10) Patent No.: US 7,635,474 B2
(45) Date of Patent: *Dec. 22, 2009

(54) VEGF-BINDING FUSION PROTEINS

(75) Inventors: Thomas J. Daly, New City, NY (US); James P. Fandl, LaGrangeville, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/135,549

(22) Filed: Jun. 9, 2008

(65) Prior Publication Data

US 2009/0062200 A1    Mar. 5, 2009

Related U.S. Application Data

(63) Continuation of application No. 11/346,008, filed on Feb. 2, 2006, now Pat. No. 7,399,612, which is a continuation-in-part of application No. 10/880,021, filed on Jun. 29, 2004, now Pat. No. 7,279,159, which is a continuation-in-part of application No. 10/609,775, filed on Jun. 30, 2003, now Pat. No. 7,087,411.

(51) Int. Cl.
*A61K 38/18* (2006.01)
*C07K 14/71* (2006.01)

(52) U.S. Cl. .................. 424/134.1; 424/192.1; 514/2; 530/350; 536/23.4

(58) Field of Classification Search ....................... None
See application file for complete search history.

(56) References Cited

U.S. PATENT DOCUMENTS

| | | | |
|---|---|---|---|
| 5,851,999 | A | 12/1998 | Ullrich et al. |
| 6,011,003 | A | 1/2000 | Charnock-Jones et al. |
| 6,100,071 | A | 8/2000 | Davis-Smyth et al. |
| 6,270,993 | B1 | 8/2001 | Shibuya et al. |
| 6,897,294 | B2 | 5/2005 | Davis-Smyth et al. |
| 2005/0281831 | A1 | 12/2005 | Davis-Smyth et al. |

FOREIGN PATENT DOCUMENTS

| WO | WO97/44453 | 11/1997 |
|---|---|---|
| WO | WO 98/13071 | 4/1998 |
| WO | WO 00/75319 | 12/2000 |

OTHER PUBLICATIONS

Holash et al., 2002, "VEGF-Trap: a VEGF blocker with potent anti-tumor effects." PNAS Aug. 20;99(17):11393-8.
Heidran et al., 1990, "Chimeric alpha- and beta-platelet-derived growth factor (PDGF) receptors define three immunoglobulin-like domains of the alpha-PDGF receptor that determine PDGF-AA binding specificity." J Biol Chem. Nov. 5;265(31):18741-4.
Cunningham et al., 1997, "Identification of the extracellular domains of Flt-1 that mediate ligand interactions." Biochem Biophys Res Commun. Feb. 24;231(3):596-9.
Fuh et al., "Requirements for binding and signaling of the kinase domain receptor for vascular endothelial growth factor." J Biol Chem. May 1;273(18):11197-204. ( 1998 ).
Wiesman et al., 1997, "Crystal structure at 1.7 A resolution of VEGF in complex with domain 2 of the Flt-1 receptor." Cell. Nov. 28;91(5):695-704.
Barleon et al., 1997, "Mapping of the sites for ligand binding and receptor dimerization at the extracellular domain of the vascular endothelial growth factor receptor FLT-1." J Biol Chem. Apr. 18;272(16):10382-8.
Davis-Smyth et al., 1998, "Mapping the charged residues in the second immunoglobulin-like domain of the vascular endothelial growth factor/placenta growth factor receptor Flt-1 required for binding and structural stability." J Biol Chem. Feb. 6;273(6):3216-22.
Wulff et al., 2002, "Prevention of thecal angiogenesis, antral follicular growth, and ovulation in the primate by treatment with vascular endothelial growth factor Trap R1R2." Endocrinology. Jul.;143(7):2797-807.
Davis-Smyth et al., 1996, "The second immunoglobulin-like domain of the VEGF tyrosine kinase receptor Flt-1 determines ligand binding and may initiate a signal transduction cascade." EMBO J. Sep. 16;15(18):4919-27.
Palu et al., 1999, "In pursuit of new developments for gene therapy of human diseases." J Biotechnol. Feb. 5;68 (1):1-13.
Wang et al., 1999, "Rapid analysis of gene expression (RAGE) facilitates universal expression profiling." Nucleic Acids Res. Dec. 1;27(23):4609-18.
Kaufman et al., 1999, Transgenic analysis of a 100-kb human B-globin cluster-containing DNA fragment propagated as a bacterial artificial chromosome. Blood 94(9): 3178-3184.
Wigley et al., 1994, "Site-specific transgene insertion: an approach." Reprod. Fertil. Dev. 6:585-588.
Wells, 1990, "Additivity of mutational effects in proteins." Biochemistry 29(37): 8509-8517.
Ngo et al., 1994, "Computational complexity, protein structure prediction, and the Levinthal paradox. In Merz and Le Grand (Eds.) The Protein Folding Problem and Tertiary Structure Prediction." Birkhauser: Boston, pp. 491-495.
Skolnick et al., 2000, "From genes to protein structure and function: novel applications of computational approaches in the genomic era." Trends in Biotechnology 18:34-39.
Phillips, 2001, "The challenge of gene therarpy and DNA delivery." Journal of Pharmacy and Pharmacology 53:1169-1174.

*Primary Examiner*—Christine J Saoud
*Assistant Examiner*—Jon M Lockard
(74) *Attorney, Agent, or Firm*—Valeta Gregg, Esq.

(57) ABSTRACT

Nucleic acid molecules encoding fusion proteins which bind and inhibit vascular endothelial growth factor (VEGF). The VEGF-binding fusion proteins are therapeutically useful for treating VEGF-associated conditions and diseases, and are specifically designed for local administration to specific organs, tissues, and/or cells.

4 Claims, No Drawings

```
                         SEQUENCE LISTING

<160> NUMBER OF SEQ ID NOS: 29

<210> SEQ ID NO 1
<211> LENGTH: 4
<212> TYPE: PRT
<213> ORGANISM: homo sapiens

<400> SEQUENCE: 1

Cys Pro Pro Cys
1

<210> SEQ ID NO 2
<211> LENGTH: 200
<212> TYPE: PRT
<213> ORGANISM: homo sapiens

<400> SEQUENCE: 2

Met Gly Arg Pro Phe Val Glu Met Tyr Ser Glu Ile Pro Glu Ile Ile
1               5                   10                  15

His Met Thr Glu Gly Arg Glu Leu Val Ile Pro Cys Arg Val Thr Ser
            20                  25                  30

Pro Asn Ile Thr Val Thr Leu Lys Lys Phe Pro Leu Asp Thr Leu Ile
        35                  40                  45

Pro Asp Gly Lys Arg Ile Ile Trp Asp Ser Arg Lys Gly Phe Ile Ile
    50                  55                  60

Ser Asn Ala Thr Tyr Lys Glu Ile Gly Leu Leu Thr Cys Glu Ala Thr
65                  70                  75                  80

Val Asn Gly His Leu Tyr Lys Thr Asn Tyr Leu Thr Gln Thr Asn Thr
                85                  90                  95

Ile Ile Asp Val Val Leu Ser Pro Ser His Gly Ile Glu Leu Ser Val
            100                 105                 110

Gly Glu Lys Leu Val Leu Asn Cys Thr Ala Arg Thr Glu Leu Asn Val
        115                 120                 125

Gly Ile Asp Phe Asn Trp Glu Tyr Pro Ser Ser Lys His Gln His Lys
    130                 135                 140

Lys Leu Val Asn Arg Asp Leu Lys Thr Gln Ser Gly Ser Glu Met Lys
145                 150                 155                 160

Lys Phe Leu Ser Thr Leu Thr Ile Asp Gly Val Thr Arg Ser Asp Gln
                170                 170                 175

Gly Thr Cys Ala Ala Ser Ser Gly Leu Met Thr Lys Lys Asn Ser Thr
                180                 185                 190

Phe Val Arg Val His Glu Lys Cys
            195                 200

<210> SEQ ID NO 3
<211> LENGTH: 4
<212> TYPE: PRT
<213> ORGANISM: homo sapiens
<220> FEATURE:
<221> NAME/KEY: VARIANT
<222> LOCATION: 1, 3
<223> OTHER INFORMATION: Xaa = Any AMino Acid

<400> SEQUENCE: 3

Xaa Cys Xaa Cys
```

<210> SEQ ID NO 4
<211> LENGTH: 4
<212> TYPE: PRT
<213> ORGANISM: homo sapiens

<400> SEQUENCE: 4

Ala Cys Gly Cys
1

<210> SEQ ID NO 5
<211> LENGTH: 203
<212> TYPE: PRT
<213> ORGANISM: homo sapiens

<400> SEQUENCE: 5

Met Gly Arg Pro Phe Val Glu Met Tyr Ser Glu Ile Pro Glu Ile Ile
1               5                  10                  15

His Met Thr Glu Gly Arg Glu Leu Val Ile Pro Cys Arg Val Thr Ser
            20                  25                  30

Pro Asn Ile Thr Val Thr Leu Lys Lys Phe Pro Leu Asp Thr Leu Ile
        35                  40                  45

Pro Asp Gly Lys Arg Ile Ile Trp Asp Ser Arg Lys Gly Phe Ile Ile
    50                  55                  60

Ser Asn Ala Thr Tyr Lys Glu Ile Gly Leu Leu Thr Cys Glu Ala Thr
65                  70                  75                  80

Val Asn Gly His Leu Tyr Lys Thr Asn Tyr Leu Thr Gln Thr Asn Thr
                85                  90                  95

Ile Ile Asp Val Val Leu Ser Pro Ser His Gly Ile Glu Leu Ser Val
            100                 105                 110

Gly Glu Lys Leu Val Leu Asn Cys Thr Ala Arg Thr Glu Leu Asn Val
        115                 120                 125

Gly Ile Asp Phe Asn Trp Glu Tyr Pro Ser Ser Lys His Gln His Lys
    130                 135                 140

Lys Leu Val Asn Arg Asp Leu Lys Thr Gln Ser Gly Ser Glu Met Lys
145                 150                 155                 160

Lys Phe Leu Ser Thr Leu Thr Ile Asp Gly Val Thr Arg Ser Asp Gln
                165                 170                 175

Gly Thr Cys Ala Ala Ser Ser Gly Leu Met Thr Lys Lys Asn Ser Thr
            180                 185                 190

Phe Val Arg Val His Glu Lys Ala Cys Gly Cys
        195                 200

<210> SEQ ID NO 6
<211> LENGTH: 6
<212> TYPE: PRT
<213> ORGANISM: homo sapiens

<400> SEQUENCE: 6

Leu Val Pro Arg Gly Ser
1               5

<210> SEQ ID NO 7
<211> LENGTH: 1453
<212> TYPE: DNA
<213> ORGANISM: homo sapiens

<400> SEQUENCE: 7

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttacttta aaaaagtttc cacttgacac tttgatccct gatggaaaac     300
gcataatctg ggacagtaga aagggcttca tcatatcaaa tgcaacgtac aaagaaatag     360
ggcttctgac ctgtgaagca acagtcaatg gcatttgta taagacaaac tatctcacac      420
atcgacaaac caatacaatc atagatgtgg ttctgagtcc gtctcatgga attgaactat     480
ctgttggaga aaagcttgtc ttaaattgta cagcaagaac tgaactaaat gtggggattg     540
acttcaactg gaatacccct tcttcgaagc atcagcataa gaaacttgta aaccgagacc     600
taaaaaccca gtctgggagt gagatgaaga aatttttgag caccttaact atagatggtg     660
taaccccgga gtgaccaagga ttgtacacct gtgcagcatc cagtgggctg atgaccaaga    720
agaacagcac atttgtcagg gtccatgaaa agggcccggg cgacaaaact cacacatgcc    780
caccgtgccc agcacctgaa ctcctggggg gaccgtcagt cttcctcttc cccccaaaac    840
ccaaggacac cctcatgatc tcccggaccc ctgaggtcac atgcgtggtg gtggacgtga    900
gccacgaaga ccctgaggtc aagttcaact ggtacgtgga cggcgtggag gtgcataatg    960
ccaagacaaa gccgcgggag gagcagtaca acagcacgta ccgtgtggtc agcgtcctca   1020
ccgtcctgca ccaggactgg ctgaatggca aggagtacaa gtgcaaggtc tccaacaaag   1080
ccctcccagc ccccatcgag aaaaccatct ccaaagccaa agggcagccc cgagaaccac   1140
aggtgtacac cctgccccca tcccgggatg agctgaccaa gaaccaggtc agcctgacct   1200
gcctggtcaa aggcttctat cccagcgaca tcgccgtgga gtgggagagc aatgggcagc   1260
cggagaacaa ctacaagacc acgcctcccg tgctggactc cgacggctcc ttcttcctct   1320
atagcaagct caccgtggac aagagcaggt ggcagcaggg gaacgtcttc tcatgctccg   1380
tgatgcatga ggctctgcac aaccactaca cgcagaagag cctctccctg tctccgggta   1440
aatgagcggc cgc                                                       1453
```

<210> SEQ ID NO 8
<211> LENGTH: 458
<212> TYPE: PRT
<213> ORGANISM: homo sapiens

<400> SEQUENCE: 8

```
Met Val Ser Tyr Trp Asp Thr Gly Val Leu Leu Cys Ala Leu Leu Ser
1               5                   10                  15

Cys Leu Leu Leu Thr Gly Ser Ser Gly Gly Arg Pro Phe Val Glu
                20                  25                  30

Met Tyr Ser Glu Ile Pro Glu Ile Ile His Met Thr Glu Gly Arg Glu
            35                  40                  45

Leu Val Ile Pro Cys Arg Val Thr Ser Pro Asn Ile Thr Val Thr Leu
        50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
                100                 105                 110
```

```
Thr Asn Tyr Leu Thr His Arg Gln Thr Asn Thr Ile Ile Asp Val Val
            115                 120                 125

Leu Ser Pro Ser His Gly Ile Glu Leu Ser Val Gly Glu Lys Leu Val
130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
            195                 200                 205

Ala Ala Ser Ser Gly Leu Met Thr Lys Lys Asn Ser Thr Phe Val Arg
210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
    450                 455
```

<210> SEQ ID NO 9
<211> LENGTH: 1377
<212> TYPE: DNA
<213> ORGANISM: homo sapiens

<400> SEQUENCE: 9

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
```

```
cctaacatca ctgttacttt aaaaaagttt ccacttgaca ctttgatccc tgatggaaaa      240
cgcataatct gggacagtag aaagggcttc atcatatcaa atgcaacgta caaagaaata      300
gggcttctga cctgtgaagc aacagtcaat gggcatttgt ataagacaaa ctatctcaca      360
catcgacaaa ccaatacaat catagatgtg ttctgagtc cgtctcatgg aattgaacta       420
tctgttggag aaagcttgt cttaaattgt acagcaagaa ctgaactaaa tgtggggatt       480
gacttcaact gggaataccc ttcttcgaag catcagcata gaaacttgt aaaccgagac       540 ctaaaaaccc agtctgggag tgagatgaag aaattttga gccacttaac tatagatggt       600
gtaacccgga gtgaccaagg attgtacacc tgtgcagcat ccagtgggct gatgaccaag      660
aagaacagca catttgtcag ggtccatgaa aaggacaaaa ctcacacatg cccaccgtgc      720
ccagcacctg aactcctggg gggaccgtca gtcttcctct ccccccaaa acccaaggac       780 accctcatga tctcccggac ccctgaggtc acatgcgtgg tggtggacgt gagccacgaa      840
gaccctgagg tcaagttcaa ctggtacgtg gacggcgtgg aggtgcataa tgccaagaca      900
aagccgcggg aggagcagta caacagcacg taccgtgtgg tcagcgtcct caccgtcctg      960
caccaggact ggctgaatgg caaggagtac aagtgcaagg tctccaacaa agccctccca     1020
gcccccatcg agaaaaccat ctccaaagcc aaagggcagc cccgagaacc acaggtgtac     1080
accctgcccc catcccggga tgagctgacc aagaaccagg tcagcctgac ctgcctggtc     1140
aaaggcttct atcccagcga catcgccgtg gagtgggaga gcaatgggca gccggagaac     1200
aactacaaga ccacgcctcc cgtgctggac tccgacggct ccttcttcct ctacagcaag     1260
ctcaccgtgg acaagagcag gtggcagcag gggaacgtct tctcatgctc cgtgatgcat     1320
gaggctctgc acaaccacta cacgcagaag agcctctccc tgtctccggg taaatga       1377
```

<210> SEQ ID NO 10
<211> LENGTH: 458
<212> TYPE: PRT
<213> ORGANISM: homo sapiens

<400> SEQUENCE: 10

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160
```

Asp Phe Asn Trp Glu Tyr Pro Ser Ser Lys His Gln His Lys Lys Leu
            165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205

Tyr Thr Cys Ala Ala Ser Ser Gly Leu Met Thr Lys Lys Asn Ser Thr
            210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
            450                 455

<210> SEQ ID NO 11
<211> LENGTH: 4
<212> TYPE: PRT
<213> ORGANISM: homo sapiens
<220> FEATURE:
<221> NAME/KEY: VARIANT
<222> LOCATION: 1, 2, 3, 4
<223> OTHER INFORMATION: Xaa = Any Amino Acid

<400> SEQUENCE: 11

Xaa Xaa Xaa Xaa
1

<210> SEQ ID NO 12
<211> LENGTH: 1444
<212> TYPE: DNA
<213> ORGANISM: homo sapiens

<400> SEQUENCE: 12

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttacttta aaaaagtttc cacttgacac tttgatccct gatggaaaac     300
gcataatctg ggacagtaga aagggcttca tcatatcaaa tgcaacgtac aaagaaatag     360
ggcttctgac ctgtgaagca acagtcaatg gcatttgta taagacaaac tatctcacac      420
atcgacaaac caatacaatc atagatatcc agctgttgcc aggaagtcg ctggagctgc      480
tggtagggga aagctggtc ctcaactgca ccgtgtgggc tgagtttaac tcaggtgtca      540
cctttgactg ggactaccca gggaagcagg cagagcgggg taagtgggtg cccgagcgac     600
gctcccaaca gacccacaca gaactctcca gcatcctgac catccacaac gtcagccagc     660
acgacctggg ctcgtatgtg tgcaaggcca acaacggcat ccagcgattt cgggagagca     720
ccgaggtcat tgtgcatgaa atggcccggg gcgacaaaac tcacacatgc caccgtgcc      780
cagcacctga actcctgggg ggaccgtcag tcttcctctt ccccccaaaa cccaaggaca     840
ccctcatgat ctcccggacc cctgaggtca catgcgtggt ggtggacgtg agccacgaag     900
accctgaggt caagttcaac tggtacgtgg acggcgtgga ggtgcataat gccaagacaa     960
agccgcggga ggagcagtac aacagcacgt accgtgtggt cagcgtcctc accgtcctgc    1020
accaggactg gctgaatggc aaggagtaca agtgcaaggt ctccaacaaa gccctcccag    1080
cccccatcga gaaaaccatc tccaaagcca aagggcagcc ccgagaacca caggtgtaca    1140
ccctgccccc atcccgggat gagctgacca agaaccaggt cagcctgacc tgcctggtca    1200
aaggcttcta tcccagcgac atcgccgtgg agtgggagag caatgggcag ccggagaaca    1260
actacaagac cacgcctccc gtgctggact ccgacggctc cttcttcctc tatagcaagc    1320
tcaccgtgga caagagcagg tggcagcagg ggaacgtctt ctcatgctcc gtgatgcatg    1380
aggctctgca caaccactac acgcagaaga gcctctccct gtctccgggt aaatgagcgg    1440
ccgc                                                                 1444
```

<210> SEQ ID NO 13
<211> LENGTH: 455
<212> TYPE: PRT
<213> ORGANISM: homo sapiens

<400> SEQUENCE: 13

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110
```

```
Thr Asn Tyr Leu Thr His Arg Gln Thr Asn Thr Ile Ile Asp Ile Gln
        115                 120                 125

Leu Leu Pro Arg Lys Ser Leu Glu Leu Leu Val Gly Glu Lys Leu Val
130                 135                 140

Leu Asn Cys Thr Val Trp Ala Glu Phe Asn Ser Gly Val Thr Phe Asp
145                 150                 155                 160

Trp Asp Tyr Pro Gly Lys Gln Ala Glu Arg Gly Lys Trp Val Pro Glu
                165                 170                 175

Arg Arg Ser Gln Gln Thr His Thr Glu Leu Ser Ser Ile Leu Thr Ile
            180                 185                 190

His Asn Val Ser Gln His Asp Leu Gly Ser Tyr Val Cys Lys Ala Asn
        195                 200                 205

Asn Gly Ile Gln Arg Phe Arg Glu Ser Thr Glu Val Ile Val His Glu
    210                 215                 220

Asn Gly Pro Gly Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 14
<211> LENGTH: 24
<212> TYPE: DNA
<213> ORGANISM: homo sapiens

<400> SEQUENCE: 14
gggctgttga gagagagaga gagc                                        24

<210> SEQ ID NO 15
```

```
<211> LENGTH: 28
<212> TYPE: DNA
<213> ORGANISM: homo sapiens

<400> SEQUENCE: 15
ggccgctctc tctctctctc aacagccc                                        28

<210> SEQ ID NO 16
<211> LENGTH: 23
<212> TYPE: DNA
<213> ORGANISM: homo sapiens

<400> SEQUENCE: 16
gggcgcatgc ggttgttgag agc                                             23

<210> SEQ ID NO 17
<211> LENGTH: 27
<212> TYPE: DNA
<213> ORGANISM: homo sapiens

<400> SEQUENCE: 17
ggccgctctc aacaaccgca tgcgccc                                         27

<210> SEQ ID NO 18
<211> LENGTH: 36
<212> TYPE: DNA
<213> ORGANISM: homo sapiens

<400> SEQUENCE: 18
gagagagacc atgggtagac ctttcgtaga gatgta                               36

<210> SEQ ID NO 19
<211> LENGTH: 48
<212> TYPE: DNA
<213> ORGANISM: homo sapiens

<400> SEQUENCE: 19
agagaggcgg ccgctttatc aacactttc atggaccctg acaaatgt                   48

<210> SEQ ID NO 20
<211> LENGTH: 57
<212> TYPE: DNA
<213> ORGANISM: homo sapiens

<400> SEQUENCE: 20
agagaggcgg ccgctttatc aacaaccgca tgccttttca tggaccctga caaatgt        57

<210> SEQ ID NO 21
<211> LENGTH: 39
<212> TYPE: DNA
<213> ORGANISM: homo sapiens

<400> SEQUENCE: 21
agttccggaa gtgccatggg tagacctttc gtagagatg                            39

<210> SEQ ID NO 22
<211> LENGTH: 44
<212> TYPE: DNA
<213> ORGANISM: homo sapiens

<400> SEQUENCE: 22
agagaggcgg ccgctgttat cacttctcgt gcacgcgcac gaag                      44
```

<210> SEQ ID NO 23
<211> LENGTH: 235
<212> TYPE: PRT
<213> ORGANISM: homo sapiens

<400> SEQUENCE: 23

```
Met Val Ser Tyr Trp Asp Thr Gly Val Leu Leu Cys Ala Leu Leu Ser
1               5                   10                  15

Cys Leu Leu Thr Gly Ser Ser Gly Ser Asp Thr Gly Arg Pro
            20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Thr Gln Ser Gly Ser Glu Met Lys Arg Asp Leu Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
210                 215                 220

Phe Val Arg Val His Glu Lys Gly Pro Gly Cys
225                 230                 235
```

<210> SEQ ID NO 24
<211> LENGTH: 435
<212> TYPE: PRT
<213> ORGANISM: homo sapiens

<400> SEQUENCE: 24

```
Met Val Ser Tyr Trp Asp Thr Gly Val Leu Leu Cys Ala Leu Leu Ser
1               5                   10                  15

Cys Leu Leu Thr Gly Ser Ser Gly Ser Asp Thr Gly Arg Pro
            20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
```

-continued

```
            100                 105                 110
Leu Tyr Lys Thr Asn Tyr Leu Thr His Arg Gln Thr Asn Thr Ile Ile
        115                 120                 125

Asp Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Gly Pro Gly Arg Pro Phe Val Glu Met
225                 230                 235                 240

Tyr Ser Glu Ile Pro Glu Ile Ile His Met Thr Glu Gly Arg Glu Leu
                245                 250                 255

Val Ile Pro Cys Arg Val Thr Ser Pro Asn Ile Thr Val Thr Leu Lys
            260                 265                 270

Lys Phe Pro Leu Asp Thr Leu Ile Pro Asp Gly Lys Arg Ile Ile Trp
        275                 280                 285

Asp Ser Arg Lys Gly Phe Ile Ile Ser Asn Ala Thr Tyr Lys Glu Ile
    290                 295                 300

Gly Leu Leu Thr Cys Glu Ala Thr Val Asn Gly His Leu Tyr Lys Thr
305                 310                 315                 320

Asn Tyr Leu Thr His Arg Gln Thr Asn Thr Ile Ile Asp Val Val Leu
                325                 330                 335

Ser Pro Ser His Gly Ile Glu Leu Ser Val Gly Glu Lys Leu Val Leu
            340                 345                 350

Asn Cys Thr Ala Arg Thr Glu Leu Asn Val Gly Ile Asp Phe Asn Trp
        355                 360                 365

Glu Tyr Pro Ser Ser Lys His Gln His Lys Lys Leu Val Asn Arg Asp
    370                 375                 380

Leu Lys Thr Gln Ser Gly Ser Glu Met Lys Lys Phe Leu Ser Thr Leu
385                 390                 395                 400

Thr Ile Asp Gly Val Thr Arg Ser Asp Gln Gly Leu Tyr Thr Cys Ala
                405                 410                 415

Ala Ser Ser Gly Leu Met Thr Lys Lys Asn Ser Thr Phe Val Arg Val
            420                 425                 430

His Glu Lys
        435

<210> SEQ ID NO 25
<211> LENGTH: 238
<212> TYPE: PRT
<213> ORGANISM: homo sapiens

<400> SEQUENCE: 25

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30
```

```
Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
 50                  55                  60

Val Thr Leu Lys Lys Phe Pro Leu Asn Thr Leu Ile Pro Asn Gly Lys
 65                  70                  75                  80

Ala Ile Ile Trp Asp Ser Arg Lys Gly Phe Ile Ile Ser Asn Ala Thr
                    85                  90                  95

Tyr Lys Glu Ile Gly Leu Leu Thr Cys Glu Ala Thr Val Asn Gly His
                100                 105                 110

Leu Tyr Lys Thr Asn Tyr Leu Thr His Arg Gln Thr Asn Thr Ile Ile
                115                 120                 125

Asp Val Val Leu Ser Pro Ser His Gly Ile Glu Leu Ser Val Gly Glu
                130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
                180                 185                 190

Leu Ser Thr Leu Thr Ile Asp Gly Val Thr Arg Ser Asp Gln Gly Leu
                195                 200                 205

Tyr Thr Cys Ala Ala Ser Ser Gly Leu Met Thr Lys Lys Asn Ser Thr
                210                 215                 220

Phe Val Arg Val His Glu Lys Gly Pro Gly Ala Cys Gly Cys
225                 230                 235

<210> SEQ ID NO 26
<211> LENGTH: 240
<212> TYPE: PRT
<213> ORGANISM: homo sapiens

<400> SEQUENCE: 26

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
 50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                    85                  90                  95

Tyr Lys Glu Ile Gly Leu Leu Thr Cys Glu Ala Thr Val Asn Gly His
                100                 105                 110

Leu Tyr Lys Thr Asn Tyr Leu Thr His Arg Gln Thr Asn Thr Ile Ile
                115                 120                 125

Asp Val Val Leu Ser Pro Ser His Gly Ile Glu Leu Ser Val Gly Glu
                130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175
```

```
Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

<210> SEQ ID NO 27
<211> LENGTH: 240
<212> TYPE: PRT
<213> ORGANISM: homo sapiens

<400> SEQUENCE: 27

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Ser Pro Pro Cys
225                 230                 235                 240

<210> SEQ ID NO 28
<211> LENGTH: 237
<212> TYPE: PRT
<213> ORGANISM: homo sapiens

<400> SEQUENCE: 28

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30
```

-continued

```
Phe Val Glu Met Tyr Ser Glu Ile Pro Glu Ile Ile His Met Thr Glu
             35                  40                  45

Gly Arg Glu Leu Val Ile Pro Cys Arg Val Thr Ser Pro Asn Ile Thr
     50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
210                 215                 220

Phe Val Arg Val His Glu Lys Asp Lys Thr His Thr Cys
225                 230                 235
```

<210> SEQ ID NO 29
<211> LENGTH: 434
<212> TYPE: PRT
<213> ORGANISM: homo sapiens

<400> SEQUENCE: 29

```
Ser Asp Thr Gly Arg Pro Phe Val Glu Met Tyr Ser Glu Ile Pro Glu
  1               5                  10                  15

Ile Ile His Met Thr Glu Gly Arg Glu Leu Val Ile Pro Cys Arg Val
             20                  25                  30

Thr Ser Pro Asn Ile Thr Val Thr Leu Lys Lys Phe Pro Leu Asp Thr
         35                  40                  45

Leu Ile Pro Asp Gly Lys Arg Ile Ile Trp Asp Ser Arg Lys Gly Phe
     50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
```

-continued

```
                165                 170                 175
Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Glu Ser Lys
        195                 200                 205

Tyr Gly Pro Pro Cys Pro Pro Cys Pro Ala Pro Glu Phe Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser Gln Glu
                245                 250                 255

Asp Pro Glu Val Gln Phe Asn Trp Tyr Val Asp Gly Val Glu Val His
            260                 265                 270

Asn Ala Lys Thr Lys Pro Arg Glu Glu Gln Phe Asn Ser Thr Tyr Arg
        275                 280                 285

Val Val Ser Val Leu Thr Val Leu His Gln Asp Trp Leu Asn Gly Lys
    290                 295                 300

Glu Tyr Lys Cys Lys Val Ser Asn Lys Gly Leu Pro Ser Ser Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Gln Glu Glu Met Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Tyr Ser Arg Leu Thr Val Asp
385                 390                 395                 400

Lys Ser Arg Trp Gln Glu Gly Asn Val Phe Ser Cys Ser Val Met His
                405                 410                 415

Glu Ala Leu His Asn His Tyr Thr Gln Lys Ser Leu Ser Leu Ser Leu
            420                 425                 430

Gly Lys
```

VEGF-BINDING FUSION PROTEINS

CROSS-REFERENCE TO RELATED APPLICATIONS

This application is a continuation of application Ser. No. 11/346,008 filed 2 Feb. 2006 now U.S. Pat. No. 7,399,612, which is a continuation-in-part of application Ser. No. 10/880,021 filed 29 Jun. 2004, now U.S. Pat. No. 7,279,159, which is a continuation-in-part of application Ser. No. 10/609,775 filed 30 Jun. 2003, now U.S. Pat. No. 7,087,411, which applications are herein specifically incorporated by reference in their entirety.

BACKGROUND OF THE INVENTION

Field of the Invention

The invention encompasses fusion proteins capable of binding vascular endothelial cell growth factor (VEGF), VEGF family members, and splice variants with specifically desirable characteristics, as well as therapeutic methods of use.

BRIEF SUMMARY OF THE INVENTION

In a first aspect, the invention features an isolated nucleic acid molecule encoding a fusion protein which binds VEGF, comprising receptor components $(R1R2)_X$ and/or $(R1R3)_Y$, wherein R1 is vascular endothelial cell growth factor (VEGF) receptor component Ig domain 2 of Flt-1 (Flt1D2), R2 is VEGF receptor component Ig domain 3 of Flk-1 (Flk1D3), and R3 is VEGF receptor component Ig domain 3 of Flt-4 (Flt1D3 or R3), and wherein $X \geq 1$ and $Y \geq 1$. In a preferred embodiment the nucleic acid molecule encodes a fusion protein comprising $(R1R2)_2$ (SEQ ID NO:24).

In a related second aspect, the invention features a monomeric VEGF-binding fusion protein comprising VEGF receptor components $(R1R2)_X$ and/or $(R1R3)_Y$ wherein $X \geq 1$, $Y \geq 1$, and R1, R2, and R3 are as defined above. The VEGF receptor components R1, R2, and R3, may be connected directly to each other or connected via one or more spacer sequences. In one specific embodiment, the fusion protein is $(R1R2)_X$, were $X=2$. In a more specific embodiment, the fusion protein is SEQ ID NO:24, or a functionally equivalent amino acid variant thereof. The invention encompasses a fusion protein consisting of VEGF receptor components $(R1R2)_X$ and/or $(R1R3)_Y$, and functionally equivalent amino acid variants thereof.

The receptor components of the VEGF-binding fusion protein may be arranged in different orders, for example, R1R2-R1R2; R2R1-R2R1; R1R2-R2R1, etc. The components of the fusion protein may be connected directly to each other, or connected via a spacer sequence. In specific embodiments, one or more receptor and/or fusion partner components of the fusion polypeptide are connected directly to each other without spacers. In other embodiments, one or more receptor and/or fusion partner components are connected with spacers.

In all embodiments of the fusion protein of the invention, a signal sequence (S) may be included at the beginning (or N-terminus) of the fusion polypeptide of the invention. The signal sequence may be native to the cell, recombinant, or synthetic. When a signal sequence is attached to the N-terminus of a first receptor component, thus a fusion polypeptide may be designated as, for example, $S-(R1R2)_X$.

The invention encompasses vectors comprising the nucleic acid molecules of the invention, including expression vectors comprising the nucleic acid molecule operatively linked to an expression control sequence. The invention further encompasses host-vector systems for the production of a fusion polypeptide which comprise the expression vector, in a suitable host cell; host-vector systems wherein the suitable host cell is a bacterial, yeast, insect, mammalian cell; an *E. coli* cell, or a COS or CHO cell. Additional encompassed are VEGF-binding fusion proteins of the invention modified by acetylation or pegylation. Methods for acetylating or pegylating a protein are well known in the art.

In a related ninth aspect, the invention features a method of producing a fusion protein of the invention, comprising culturing a host cell transfected with a vector comprising a nucleic acid sequence of the invention, under conditions suitable for expression of the protein from the host cell, and recovering the fusion polypeptides so produced.

The VEG-binding fusion proteins of the invention are therapeutically useful for treating any disease or condition which is improved, ameliorated, or inhibited by removal, inhibition, or reduction of VEGF. A non-exhaustive list of specific conditions improved by inhibition or reduction of VEGF include, for example, undesirable plasma leakage or vascular permeability, undesirable blood vessel growth, e.g., such as in a tumor, edema associated with inflammatory disorders such as psoriasis or arthritis, including rheumatoid arthritis; asthma; generalized edema associated with burns; ascites and pleural effusion associated with tumors, inflammation or trauma; chronic airway inflammation; asthma; capillary leak syndrome; sepsis; kidney disease associated with increased leakage of protein; pancreatic ductal adenocarcinoma (PDAC) and eye disorders such as age related macular degeneration and diabetic retinopathy. The fusion protein of the invention is particularly useful in treatment of eye disorders, and as an adjuvant to eye surgeries, including glaucoma surgery; and the treatment of intra-ocular tumors, such as for example, uveal melanoma, retinoblastoma, via intravitreal delivery.

Accordingly, in a tenth aspect, the invention features a therapeutic method for the treatment of a VEGF-related disease or condition, comprising administering a VEGF-binding fusion protein of the invention to a subject suffering from a VEGF-related disease or condition. Although any mammal can be treated by the therapeutic methods of the invention, the subject is preferably a human patient suffering from or at risk of suffering from a condition or disease which can be improved, ameliorated, inhibited or treated with a VEGF trap.

In a eleventh aspect, the invention further features diagnostic and prognostic methods, as well as kits for detecting, quantitating, and/or monitoring VEGF with the fusion proteins of the invention.

In a twelfth aspect, the invention features pharmaceutical compositions comprising a VEGF-binding fusion protein of the invention with a pharmaceutically acceptable carrier. Such pharmaceutical compositions may comprise a fusion protein or a nucleic acid encoding the fusion protein.

Other objects and advantages will become apparent from a review of the ensuing detailed description.

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

General Description

The invention encompasses a fusion protein capable of binding and inhibiting VEGF activity. The molecules of the invention bind and inhibit the biological action of VEGF and/or the physiological reaction or response. For a description of VEGF-receptor-based antagonist VEGF traps Flt1D2.Flk1D3.FcΔC1(a) (SEQ ID NOs:7-8) and VEGFR1R2-FcΔC1(a) (SEQ ID NOs:9-10), see PCT WO/0075319, the contents of which is incorporated in its entirety herein by reference. The fusion proteins of the invention are smaller than the full sized trap, e.g., about 50-60 kD versus 120 kD of the parent trap, and are monomers. As shown in the experimental section below, the fusion proteins of the invention exhibit unique kinetic properties yet retain a high binding affinity to VEGF.

Nucleic Acid Constructs and Expression

The present invention provides for the construction of nucleic acid molecules encoding fusion proteins capable of binding VEGF. The nucleic acid molecules of the invention may encode wild-type R1, R2, and/or R3 receptor components, or functionally equivalent variants thereof. Amino acid sequence variants of the R1, R2 and/or R3 receptor components of the traps of the invention may also be prepared by creating mutations in the encoding nucleic acid molecules. Such variants include, for example, deletions from, or insertions or substitutions of, amino acid residues within the amino acid sequence of R1, R2 and/or R3. Any combination of deletion, insertion, and substitution may be made to arrive at a final construct, provided that the final construct possesses the ability to bind and inhibit VEGF.

These nucleic acid molecules are inserted into a vector that is able to express the fusion proteins of the invention when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the invention under control of transcriptional/translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the β-lactamase promoter, or the tac promoter (see also Scientific American (1980) 242:74-94); promoter elements from yeast or other fungi such as Gal 4 promoter, ADH, PGK, alkaline phosphatase, and tissue-specific transcriptional control regions derived from genes such as elastase 1.

Expression vectors capable of being replicated in a bacterial or eukaryotic host comprising the nucleic acid molecules of the invention are used to transfect the host and thereby direct expression of such nucleic acids to produce the fusion proteins of the invention which bind and inhibit VEGF. Transfected cells may transiently or, preferably, constitutively and permanently express the fusion proteins of the invention.

VEGF Receptor Components

The VEGF receptor components of the fusion proteins of the invention consist of the Ig domain 2 of Flt-1 (Flt1D2) (R1), the Ig domain 3 of Flk-1 (Flk1D3) (R2) (together, R1R2), and/or R1 and Ig domain 3 of Flt-4 (Flt1D3) (R3) (together, R1R3). The term "Ig domain" of Flt-1, Flt-4, or Flk-1 is intended to encompass not only the complete wild-type domain, but also insertional, deletional, and/or substitutional variants thereof which substantially retain the functional characteristics of the intact domain. It will be readily apparent to one of skill in the art that numerous variants of the above Ig domains can be obtained which will retains substantially the same functional characteristics as the wild-type domain.

The term "functional equivalents" when used in reference to R1, R2, or R3, is intended to encompass an R1, R2, or R3 domain with at least one alteration, e.g., a deletion, addition, and/or substitution, which retains substantially the same functional characteristics as does the wild type R1, R2, or R3 domain, that is, a substantially equivalent binding to VEGF. It will be appreciated that various amino acid substitutions can be made in R1, R2, or R3 without departing from the spirit of the invention with respect to the ability of these receptor components to bind and inactivate VEGF. The functional characteristics of the traps of the invention may be determined by any suitable screening assay known to the art for measuring the desired characteristic. Examples of such assays are described in the experimental section below which allow determination of binding characteristics of the traps for VEGF (Kd), as well as their half-life of dissociation of the trap-ligand complex ($T_{1/2}$). Other assays, for example, a change in the ability to specifically bind to VEGF can be measured by a competition-type VEGF binding assay. Modifications of protein properties such as thermal stability, hydrophobicity, susceptibility to proteolytic degradation, or tendency to aggregate may be measured by methods known to those of skill in the art.

The components of the fusion polypeptide may be connected directly to each other or be connected via spacers. Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the fusion polypeptide from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the fusion polypeptides, provide specifically desired sites of interest, allow component domains to form optimal tertiary structures and/or to enhance the interaction of a component with its target molecule. In one embodiment, the spacer comprises one or more peptide sequences between one or more components which is (are) between 1-100 amino acids, preferably 1-25.

In the most specific embodiments, R1 is amino acids 27-126 of SEQ ID NO:8, or 1-126 of SEQ ID NO:8 (including the signal sequence 1-26); or amino acids 27-129 of SEQ ID NO:10, or 1-129 of SEQ ID NO:10 (including the signal sequence at 1-26). In the most specific embodiments, R2 is amino acids 127-228 of SEQ ID NO:8, or amino acids 130-231 of SEQ ID NO:10. In the most specific embodiments, R3 is amino acids 127-225 of SEQ ID NO: 13 (without a signal sequence). When, for example, R2 is placed at the N-terminus of the fusion polypeptide, a signal sequence may desirably precede the receptor component. The receptor component(s) attached to the multimerizing component may further comprise a spacer component, for example, the GPG sequence of amino acids 229-231 of SEQ ID NO:7.

Therapeutic Uses

The VEGF-binding fusion proteins of the invention are therapeutically useful for treating any disease or condition which is improved, ameliorated, inhibited or prevented by removal, inhibition, or reduction of VEGF. A non-exhaustive list of specific conditions improved by inhibition or reduction of VEGF include, clinical conditions that are characterized by excessive vascular endothelial cell proliferation, vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

The compositions of the invention are therapeutically useful for treating a wide variety of diseases associated with increased VEGF levels. For example, exaggerated Th2 inflammation and airway remodeling are characteristic in the pathogenesis of asthma (see, for example, Elias et al. (1999) J. Clin. Invest. 104:1001-6). Elevated VEGF levels have been detected in tissues and biologic samples from patients with asthma, which correlate directly with disease activity (Lee et al. (2001) J. Allergy Clin. Immunol. 107:1106-1108) and inversely with airway caliber and airway responsiveness. Further, VEGF has been postulated to contribute to asthmatic tissue edema.

Another disease associated with increased VEGF is pancreatic ductal adenocarcinoma (PDAC). This malignancy often exhibits enhanced foci of endothelial cell proliferation and frequently overexpresses VEGF (Ferrara (1999) J. Mol. Med. 77:527-543). PDAC is responsible for over 20% of deaths due to gastrointestinal malignancies, making it the fourth most common cause of cancer-related mortality in the U.S. and other industrialized countries. Experimental evidence supports an important role for VEGF in pancreatic cancer, thus a VEGF inhibitor has promise as a therapeutic to attenuate intrapancreatic tumor growth and regional and distal metastasis.

The fusion proteins of the invention differ from larger VEGF antagonists in being optimized for local/intra-vitreal delivery, ie. a shorter serum half life for faster clearance and minimizing unwanted systemic exposure. In addition due to its smaller size, the fusion proteins of the invention have the ability to penetrate through the inner-limiting membrane (ILM) in the eye, and diffuse through the vitreous to the retina/retinal pigment epithelial (RPE) layer which will help to treat retinal disease. Additionally, the fusion proteins of the invention can be used for local administration for the treatment of ocular disease such as choroidal neovascularization, diabetic macular edema, proliferative diabetic retinopathy, corneal neovascularization/transplant rejection. Still further, the mini-trap can be used in any situation where transient (short-term) blocking of VEGF is required, e.g., to avoid chronic exposure to VEGF blockade, such as, for example, in the treatment of psoriasis.

A serious problem leading to failure following glaucoma surgery is early inflammation and angiogenesis, as well as too aggressive wound healing. Accordingly, the VEGF-binding fusion proteins of the invention may be usefully employed is as an adjuvant to glaucoma surgery to prevent early hem- and lymphangiogenesis and macrophage recruitement to the filterig bleb after glaucoma surgery, and improve surgical outcome.

Combination Therapies

In numerous embodiments, the fusion protein of the invention may be administered in combination with one or more additional compounds or therapies, including a second VEGF-binding molecule, a chemotherapeutic agent, surgery, catheter devices, and radiation. Combination therapy includes administration of a single pharmaceutical dosage formulation which contains the fusion protein of the invention and one or more additional agents; as well as administration of a the fusion protein of the invention and one or more additional agent(s) in its own separate pharmaceutical dosage formulation. For example, a fusion protein and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion polypeptide of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Methods of Administration

The invention provides methods of treatment comprising administering to a subject an effective amount of a VEGF-binding fusion protein of the invention. In a preferred aspect, the trap is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment. Further, the composition can take the form of a solid article that can be inserted in the eye, such as for example between the eye and eyelid or in the conjunctival sac, where the VEGF trap is released. Release from such an article is usually to the cornea, either via the lacrimal fluid, or directly to the cornea itself, with which the solid article is generally in direct contact. Solid articles suitable for implantation in the eye are generally composed primarily of bioerodible or nonbioerodible polymers. An aqueous solution and/or suspension can be in the form of eye drops. A desired dosage of the active agent can be measured by administration of a known number of drops into the eye. For example, for a drop volume of 25 μl, administration of 1-6 drops will deliver 25-150 μl of the composition.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous or mucoadhesive.

In another embodiment, the composition useful in practicing the methods of the invention is an in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye.

Diagnostic and Screening Methods

The fusion proteins of the invention may be used diagnostically and/or in screening methods. For example, the trap may be used to monitor levels of VEGF during a clinical study to evaluate treatment efficacy. In another embodiment, the methods and compositions of the present invention are used to screen individuals for entry into a clinical study to identify individuals having, for example, too high or too low a level of VEGF. The fusion proteins can be used in methods known in the art relating to the localization and activity of VEGF, e.g., imaging, measuring levels thereof in appropriate physiological samples, in diagnostic methods, etc.

The fusion proteins of the invention may be used in in vivo and in vitro screening assay to quantify the amount of non-bound VEGF present, e.g., for example, in a screening method to identify test agents able to decrease the expression of VEGF. More generally, the fusion proteins of the invention may be used in any assay or process in which quantification and/or isolation of VEGF is desired.

Pharmaceutical Compositions

The present invention also provides pharmaceutical compositions comprising a fusion protein of the invention. Such compositions comprise a therapeutically effective amount of one or more fusion proteins, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The fusion protein of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Further more, aqueous compositions useful for practicing the methods of the invention have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers are included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The amount of the fusion protein that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 50-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Cellular Transfection and Gene Therapy

The present invention encompasses the use of nucleic acids encoding the fusion proteins of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing VEGF levels in a human or other animal comprising transfecting a cell with a nucleic acid encoding a fusion protein of the invention, wherein the nucleic acid comprises an inducible promoter operably linked to the nucleic acid encoding the fusion protein. For gene therapy procedures in the treatment or prevention of human disease, see for example, Van Brunt (1998) Biotechnology 6:1149-1154.

Kits

The invention also provides an article of manufacturing comprising packaging material and a pharmaceutical agent contained within the packaging material, wherein the pharmaceutical agent comprises at least one VEGF-binding fusion protein of the invention, and wherein the packaging material comprises a label or package insert which indicates that the VEGF-specific fusion protein can be used for treating a VEGF-mediated disease or condition.

Transgenic Animals

The invention includes transgenic non-human animals expressing a fusion protein of the invention. A transgenic animal can be produced by introducing nucleic acid into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells. A transgenic non-human animal expressing a fusion protein of the invention is useful in a variety of applications, including as a means of producing such a fusion protein. Further, the transgene may be placed under the control of an inducible promoter such that expression of the fusion protein may be controlled by, for example, administration of a small molecule.

SPECIFIC EMBODIMENTS

In the experiments described below, smaller VEGF traps were generated and their ability to bind VEGF was investigated. Such mini-traps are preferably uses in specific applications. For example, certain conditions or diseases may be preferably treated with local administration of a VEGF trap to a specific organ, tissue, or cell, rather than by systemic administration. In one exemplification of the mini-traps of the invention, a smaller VEGF trap was generated by directed cleavage of a dimerized VEGF trap having a cleavage region (C-region) generated in a Fc domain (Example 2). The truncated trap exhibited comparable affinity for VEGF and half-life as the full-sized parent trap. Examples 3-5 describe construction of fusion polypeptides having a VEGF receptor component and a multimerizing component consisting of one or two cysteine residues. Affinity measurements showed that the non-glycosylated fusion polypeptides expressed in E. coli or the glycosylated polypeptides expressed in CHO cells had comparable binding affinity for VEGF as the full-sized parent trap. Example 6 further illustrates a monomeric VEGF trap consisting of (R1R2)$_2$ (SEQ ID NO:24) which is capable of binding and inhibiting VEGF. Example 7 describes the construction of a VEGF mini-trap (SEQ ID NO:26) exhibiting high affinity binding for VEGF comparable to the full length trap (SEQ ID NO:10). Example 8 provides pharmacokinetic data of the fusion protein of SEQ ID NO:24.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of Flt1D2.Flk1D3.FcΔC1(a)

The construction of a parent VEGF trap, Flt1D2.Flk1D3.FcΔC1(a) (SEQ ID NOs:7-8), VEGFR1R2.FcΔC1(a) (SEQ ID NOs:9-10), and Flt1D2.VEGFR3D3.FcΔC1(a) (SEQ ID NOs:12-13) is described in detail in PCT publication WO/0075319, herein specifically incorporated by reference in its entirety. Also described in WO/0075319 are methods of constructing and expressing nucleic acid constructs encoding VEGF traps, methods of detecting and measuring VEGF trap binding to VEGF, methods of determining the stoichiometry of VEGF binding by BIACORE® analysis, and pharmacokinetic analyses.

Example 2

Thrombin-Cleaved Dimeric VEGF Mini-Trap

The VEGFR1R2.FcΔC1(a) (SEQ ID NOs:9-10) construct was modified by insertion of a thrombin cleavage following the CPPC (SEQ ID NO:1) of the Fc domain. Purified VEGF trap (5 µg) was incubated with thrombin (Novagen) in 20 mM Tris-HCl, pH 8.4, 50 mM NaCl, 2.5 mM CaCl$_2$ for 16 hrs at 37° C. Controls included cleavage control protein (CCP) and parent VEGF trap protein incubated without thrombin. SDS-PAGE analysis (Tris-Glycine 4-20% gel; 5 µg protein per lane) verified correct cleavage (results not shown).

Affinity determination. The Kd of binding of each VEGF trap to hVEGF165 was determined as described in WO/0075319, for the parent VEGF trap, uncleaved VEGF trap containing a thrombin cleavage site ("uncleaved VEGF trap"), cleaved VEGF mini-trap and recombinant monomeric R1R2-myc myc his. More specifically, the ability of the traps to block VEGF$_{165}$-dependent receptor phosphorylation was determined using primary human endothelial cells (HUVECs). VEGF$_{165}$ was incubated in the presence of varying concentrations of the test traps, and the mixture was added to HUVECs to stimulate tyrosine phosphorylation of VEGFR2. At sub-stoichiometric concentrations of VEGF trap, unbound VEGF induced receptor phosphorylation. However, at a 1:1 molar ratio of greater of a VEGF trap to ligand, complete blocking of receptor signaling was observed, establishing that a single molecule of a trap dimer is capable of blocking a single molecule of human VEGF$_{165}$. Thus, the high binding affinity of the VEGF trap for VEGF results in formation of a complex that prevents VEGF from interaction with cell surface receptors. Equivalent results were obtained for identical phosphorylation inhibition experiments for the parent VEGF trap, uncleaved VEGF trap, and cleaved VEGF mini-trap The results are shown in Table 1.

TABLE 1

| Trap | Kinetic Dissociation Rate (1/s) | $T_{1/2}$ (hr) |
|---|---|---|
| parent VEGF trap | $5.51 \times 10^{-5} \pm 0.94\%$ | 3.5 |
| uncleaved VEGF trap | $4.93 \times 10^{-5} \pm 0.70\%$ | 3.9 |
| cleaved VEGF mini-trap | $5.46 \times 10^{-5} \pm 0.62\%$ | 3.53 |
| R1R2-myc myc his monomer | $6.74 \times 10^{-3} \pm 0.38\%$ | 0.028 |

Example 3

Construction of Plasmids Encoding VEGF Mini-Traps

VEGF mini-traps were constructed from a precursor of the parent VEGF trap, VEGFR1R2.FcΔC1(a) (SEQ ID NOs:9-10), in which the three amino acids glycine-alanine-proline served as a linker between the Flk1D3 and FcΔC1(a). This plasmid, pTE115 was used in the construction of the VEGF mini-traps because the linker DNA sequence included a Srf I restriction endonuclease recognition sequence that facilitated engineering the VEGF trap. In all other respects, the VEGF trap encoded by pTE115 is identical to that of the VEGF trap, VEGFR1R2.FcΔC1(a) (SEQ ID NOs:9-10) described in detail in PCT publication WO/0075319.

Two VEGF mini-traps were constructed with multimerization domains consisting of either a single cysteine residue (R1R2$_C$) (SEQ ID NO:2) or the amino acids ACGC (SEQ ID NO:4) (R1R2$_{ACGC}$) (SEQ ID NO:5) added to the C-terminus of receptor components Flt1D2.Flk1D3. Both of these constructs are capable of forming homo-dimeric molecules stabilized by one (R1R2$_C$) or two (R1R2$_{ACGC}$) intermolecular disulfides.

The plasmid pTE517 was made by removing the 690 bp fragment generated by digestion of pTE115 DNA with Srf I and Not I and inserting the synthetic DNA fragment formed by annealing the oligos R1R2NC (SEQ ID NO:14) and R1R2CC (SEQ ID NO:15). The resulting plasmid encodes R1R2$_C$, which consists of the Flt1D2.Flk1D3 domains followed by a cysteine residue (SEQ ID NO:23). Similarly, the plasmid pTE518 was made by removing the 690 bp fragment generated by digestion of pTE115 DNA with Srf I and Not I, followed by ligation with the synthetic DNA fragment formed by annealing the oligos R1R2NACGC (SEQ ID NO:16) and R1R2CACGC (SEQ ID NO:17). The resulting plasmid encodes R1R2$_{ACGC}$, which consists of the Flt1D2.Flk1D3 domains followed by the amino acids ACGC (SEQ ID NO:25).

Plasmids were also constructed to direct the expression of these mini-traps in E. coli. The primers R1R2N-Ncol (SEQ ID NO:18) and R1R2CNot1 (SEQ ID NO:19) were used to amplify a DNA fragment from pTE115 that encodes amino acids G30 to K231, relative to the parental VEGF trap (SEQ ID NO:10). Amplification of this sequence resulted in fusion of an initiating methionine codon at the 5' end and fusion of the codon for cysteine, followed by a stop codon, at the 3' end (SEQ ID NO:2). This DNA fragment was then cloned into the Nco I and Not I sites of the E. coli expression plasmid pRG663 to yield pRG1102 such that expression of R1R2$_C$ was dependent on transcription from the phage T7 Φ1.1 promoter. Induction of gene expression from pRG1102 results in accumulation of R1R2cys in the cytoplasm of the E. coli host strain RFJ238. Similarly, the primers R1R2N-Ncol (SEQ ID NO:18) and R1R2ACGC-N ot1 (SEQ ID NO:20) were used to amplify a DNA fragment from pTE115 that encodes amino acids G30 to K231 (SEQ ID NO:10) resulting in fusion of an initiating methionine codon at the 5' end and fusion of codons for ACGC (SEQ ID NO:4), followed by a stop codon, at the 3' end (SEQ ID NO:5). This fragment was then cloned into the Nco I and Not I sites of the E. coli expression plasmid pRG663 to yield pRG1103 such that expression of R1R2$_{ACGC}$ was dependent on transcription from the phage T7 Φ1.1 promoter. Induction of gene expression from both pRG1102 and pRG1103 resulted in accumulation of R1R2$_C$ or R1R2$_{ACGC}$, respectively, in the cytoplasm of the E. coli host strain RFJ238.

Example 4

Purification and Characterization of VEGF Mini-Traps from E. coli

Both R1R2$_C$ and R1R2$_{ACGC}$ were expressed as cytoplasmic proteins in E. coli and were purified by the same method. Induction of the phage T7 Φ1.1 promoter on either pRG1102 or pRG1103 in the E. coli K12 strain RFJ238 resulted in accumulation of the protein in the cytoplasm. After induction, cells were collected by centrifugation, resuspended in 50 mM Tris-HCl, pH 7.5, 20 mM EDTA, and lysed by passage through a Niro-Soavi cell homogenizer. Inclusion bodies were collected from lysed cells by centrifugation, washed once in distilled H$_2$O, then solubilized in 8 M guanidinium-HCl, 50 mM Tris-HCl, pH 8.5, 100 mM sodium sulfite, 10 mM sodium tetrathionate and incubated at room temperature for 16 hours. Clarified supernatant was fractionated on an S300 column equilibrated with 6 M guanidinium-HCl, 50 mM Tris-HCl, pH 7.5. Fractions containing R1R2$_C$ were pooled and dialyzed against 6M Urea, 50 mM Tris-HCl, pH 7.5. Dialyzed protein was diluted to 2M Urea, 50 mM Tris-HCl, pH 8.5, 2 mM cysteine then stirred slowly for 7 days at 4° C. Refolded protein was dialyzed against 50 mM Tris-HCl, pH 7.5 then loaded onto an SP-sepharose column equilibrated with 50 mM Tris-HCl, pH 7.5 and eluted with a NaCl gradient from 0 to 1 M in 50 mM Tris-HCl, pH 7.5. Fractions containing R1R2$_C$ were pooled, concentrated, and loaded onto a Superdex 200 column equilibrated with 50 mM Tris-HCl, pH 7.5, 150 mM NaCl. Fractions containing mini-trap dimer were collected and pooled. The molecular weight of purified mini-trap was estimated to be about 46 kD by SDS-PAGE.

BIACORE® (surface plasmon resonance) assays were conducted (as described in WO/0075319) to determine trap affinity for VEGF, and the results showed that the R1R2$_C$ and R1R2$_{ACGC}$ mini-traps had VEGF affinity comparable to the full length VEGF trap (Table 2).

TABLE 2

| Trap | Kinetic Dissociation Rate (1/s) | $T_{1/2}$ (hr) |
|---|---|---|
| VEGF trap | $4.23 \times 10^{-5}$ | 4.53 |
| $R1R2_C$ | $3.39 \times 10^{-5}$ | 5.68 |
| $R1R2_{ACGC}$ | $3.41 \times 10^{-5}$ | 5.65 |

Example 5

Expression of VEGF Mini-Traps in CHO K1

Expression of the VEGF mini-traps encoded by pTE517 and pTE518 is dependent on transcription from the human CMV-MIE promoter and results in secretion of the mini-traps into the culture medium when expressed in CHO cells. When expressed as secreted proteins in CHO K1, both mini-traps were found in the conditioned media and estimation of their molecular weight by SDS-PAGE suggested, as expected, that the proteins were glycosylated. Analysis by SDS-PAGE also indicated that the mini-traps were capable of forming homo-dimeric molecules stabilized by intermolecular disulfide(s) between the C-terminal cysteine(s). Specifically, the $R1R2_C$ mini-trap efficiently formed covalent dimers when expressed as a secreted protein in CHO cells.

Example 6

Construction and Expression of a Single Chain VEGF Mini-Trap

A VEGF mini-trap was also constructed that did not require a multimerization domain (SEQ ID NO:24). This mini-trap was constructed by direct fusion of one Flt1D2.Flk1D3 domain (R1R2) (amino acids 30-231 of SEQ ID NO:24) to a second Flt1D2.Flk1D3 domain (R1R2) (amino acids 234-435 of SEQ ID NO:24) with a Gly-Pro linker between the tandem receptor domains (amino acids 232-233 of SEQ ID NO:24).

To construct a gene encoding tandem Flt1D2.Flk1D3 domains, a DNA fragment was synthesized (Blue Heron Biotechnology) that encoded one Flt1D2.Flk1D3 domain that minimized DNA homology with the Flt1D2.Flk1D3 domain-encoding DNA found in pTE115. This synthetic DNA fragment was cloned as a Srf I-Not I fragment into the Srf I-Not I sites of pTE115 to yield pTE570, which expresses the R1R2-R1R2 VEGF mini-trap from the CMV-MIE promoter. When this plasmid is transfected into CHO K1 cells the R1R2-R1R2 VEGF mini-trap accumulates in the culture medium.

Example 7

Construction and Expression of a VEGF Mini-Trap

A VEGF mini-trap was constructed as described above, by direct fusion of one Flt1D2.Flk1D3 domain (R1R2) (amino acids 30-231 of SEQ ID NO:26) with a C-terminal nine amino acid sequence terminating in CPPC. When this plasmid is transfected into CHO K1 cells the VEGF mini-trap of SEQ ID NO:26 is secreted into the culture medium. Subsequent purification by non-reducing SDS-PAGE electrophoresis as well as native light-scattering analysis identified a trap molecule with molecular weight approximately 64 kDa. This molecular weight indicates that a covalent dimer was formed between two fusion polypeptides of SEQ ID NO:26. Similar experiments were conducted with plasmids encoding the fusion polypeptides of SEQ ID NOS:27 and 28, and similarly showed these molecules formed homodimeric traps. Affinity determinations for human VEGF-165 binding to VEGF traps composed of dimers of SEQ ID NO:10 and SEQ ID NO:26 are shown in Table 3.

TABLE 3

| VEGF Trap | ka (1/Ms) | kd (1/s) | KD (M) |
|---|---|---|---|
| SEQ ID NO: 10 | $2.73 \times 10^{+7}$ | $1.79 \times 10^{-5}$ | $6.55 \times 10^{-13}$ |
| SEQ ID NO: 26 | $2.00 \times 10^{+7}$ | $6.56 \times 10^{-6}$ | $3.28 \times 10^{-13}$ |
| SEQ ID NO: 26 | $2.61 \times 10^{+7}$ | $5.77 \times 10^{-6}$ | $2.21 \times 10^{-13}$ |

Example 8

Kinetics of Fusion Protein R1R2R1R2 (SEQ ID NO:24)

Following the expression of fusion protein R1R2R1R2 (SEQ ID NO:24) described in Example 6 above, the fusion protein was purified by standard techniques using ion exchange chromatography followed by size exclusion chromatography.

An affinity analysis of each candidate fusion protein was performed on a BIACORE®2000 (Biacore, Inc., Piscataway, N.J.) with HBS-T and 0.005 percent P20 surfactant (Biacore, Inc.) as running buffer. Anti-VEGFR1 monoclonal antibody (P3 mAb) was immobilized to a research grade CM5 sensor chip (Biacore, Inc.) via primary amine groups using the Amine Coupling Kit (Biacore, Inc.) according to the manufacturer's suggested protocol.

Binding assays were carried out by first capturing around 100 RU of each fusion protein construct to the immobilized anti-VEGFR1 mAb, after which various concentrations (0-2 nM) of human VEGF165 were injected over the captured fusion protein surface at a flow rate of 100 μl/min for 2 minutes. The fusion protein constructs binding kinetic parameters including ka (1/Ms) (association rate constant), kd (1/s) (dissociation rate constant) and KD (dissociation equilibrium constant) were determined using the BIA evaluation 4.1 computer program (Biacore, Inc.), and t1/2 was determined using formula 0.693/kd (dissociation rate).

TABLE 3

Comparison of Kinetic Profiles for Two Different Fusion Protein Constructs

| | RU Captured | kd (1/s) | ka (1/Ms) | KD (M) | t ½ (hr) |
|---|---|---|---|---|---|
| SEQ ID NO: 26 | 96 | $5.06 \times 10^{-6}$ | $5.62 \times 10^{+6}$ | $9.01 \times 10^{-13}$ | 38.07 |
| SEQ ID NO: 24 | 94 | $8.00 \times 10^{-6}$ | $4.54 \times 10^{+6}$ | $1.76 \times 10^{-12}$ | 24.08 |

Other features of the invention will become apparent in the course of the following descriptions of exemplary embodiments which are given for illustration of the invention and are not intended to be limiting thereof.

We claim:

1. An article of manufacturing comprising packaging material and a pharmaceutical agent contained within the packaging material, wherein the pharmaceutical agent comprises at least one vascular endothelial growth factor (VEGF)-binding fusion protein and the VEGF-binding fusion protein consists of R1, R2, and a multimerizing component (MC) wherein R1 is VEGF receptor component Ig domain 2 of Flt-1 consisting of amino acids 27-126 of SEQ ID NO:8 or 27-129 of SEQ ID NO: 10, R2 is Ig domain 3 of Flk-1 consisting of amino acids 127-228 of SEQ ID NO: 8 or 130-231 of SEQ ID NO:10, and MC comprises the amino acid sequence of SEQ ID NO:11.

2. The article of claim 1, wherein the MC comprises an amino acid sequence selected from the group consisting of SEQ ID NO:1, SEQ ID NO:3 and SEQ ID NO:4.

3. The article of claim 2, wherein the VEGF-binding fusion protein comprises the amino acid sequence shown in SEQ ID NO:26.

4. The article of claim 2, wherein the VEGF-binding fusion protein comprises the amino acid sequence shown in SEQ ID NO:5.

* * * * *